United States Patent
Sun et al.

(10) Patent No.: US 12,110,563 B1
(45) Date of Patent: Oct. 8, 2024

(54) MULTIPLE LAMP PRIMER SET, DETECTION METHOD, AND KIT FOR SIMULTANEOUS DETECTION OF MULTIPLE PATHOGENS

(71) Applicant: HAINAN UNIVERSITY, Haikou (CN)

(72) Inventors: Yun Sun, Haikou (CN); Zhenjie Cao, Haikou (CN); Yongcan Zhou, Haikou (CN); Tao Li, Haikou (CN); Ying Wu, Haikou (CN); Hehe Du, Haikou (CN); Weiliang Guo, Haikou (CN); Shifeng Wang, Haikou (CN)

(73) Assignee: HAINAN UNIVERSITY, Haikou (CN)

( * ) Notice: Subject to any disclaimer, the term of this patent is extended or adjusted under 35 U.S.C. 154(b) by 0 days.

(21) Appl. No.: 18/425,327

(22) Filed: Jan. 29, 2024

(30) Foreign Application Priority Data

May 29, 2023 (CN) .......................... 202310611140.1

(51) Int. Cl.
*C12Q 1/689* (2018.01)
*C12Q 1/6844* (2018.01)
*C12Q 1/70* (2006.01)

(52) U.S. Cl.
CPC ........... *C12Q 1/689* (2013.01); *C12Q 1/6844* (2013.01); *C12Q 1/701* (2013.01); *C12Q 2600/16* (2013.01)

(58) Field of Classification Search
CPC ...... C12Q 1/689; C12Q 1/6844; C12Q 1/701; C12Q 2600/16
See application file for complete search history.

(56) References Cited

FOREIGN PATENT DOCUMENTS

CN 111778363 A * 10/2020 ........... C12Q 1/6844

OTHER PUBLICATIONS

Rahman, A. et al Improvements to the rapid detection of the marine pathogenic bacterium, V. harveyi, using loop-mediated isothermal amplification in combination with SYBR green.2022. Microrganisms. 10:2346. (Year: 2022).*
Teh, TRD et al. Detection of V. parahaemolyticus in fish samples from selected wet markets in Laguna, Phillipines, using loop-mediated isothermal amplification and real-time polymerase chain reaction. 2020. Philippine Science Letters, 13, 84-91. (Year: 2020).*
Yu, Y. et al LAMP for the rapid diagnosis of iridovirus in aquaculture. 2022. Aquaculture and Fisheries. 7:158-165. (Year: 2022).*

(Continued)

*Primary Examiner* — Samuel C Woolwine
*Assistant Examiner* — Lisa Horth
(74) *Attorney, Agent, or Firm* — Jeenam Park

(57) ABSTRACT

The present disclosure relates to a multiple LAMP primer set, a detection method, and a kit for simultaneously detecting multiple pathogens, belonging to the field of microbial detection. The multiple pathogens are *Vibrio harveyi*, *Vibrio parahaemolyticus*, and Singapore grouper iridovirus. The detection primer set is as shown in SEQ ID NO.: 1-18. The present disclosure further provides an application, a kit, and a detection method of multiple LAMP primer sets in simultaneously detecting multiple pathogens. The method of the present disclosure can simultaneously detect whether a sample contains the *Vibrio harveyi*, the *Vibrio parahaemolyticus*, or the Singapore grouper iridovirus, has strong specificity, convenient and simple operation, and has no need for an expensive instrument and equipment.

2 Claims, 2 Drawing Sheets

Specification includes a Sequence Listing.

(56) References Cited

OTHER PUBLICATIONS

Liu, N. et al. Development of a multiplex loop-mediated isothermal amplification method for the simultaneous detection of *Salmonella* spp. and *Vibrio parahaemolyticus*. 2017. Sci Reports. 7:45601 (Year: 2017).*

Abdullah, A. et al. The presence of Vibrionaceae, Betanodavirus and Iridovirus in marine cage-cultured fish: role of fish size, water, physiochemical parameters and relationships among the pathogens. Aquaculture Reports 7: 57-65. (Year: 2017).*

Tomita et al. Loop-mediated isothermal amplification (LAMP) of gene sequences and simple visual detection of products. Nature Protocols 3(5):877-882 (2008). (Year: 2008).*

Abdullah A. et al. The presence of Vibrionaceae, Betanodavirus and Iridovirus in marine cage-cultured fish: Role of fish size, water physiochemical parameters and relationships among the pathogens. 2017. Aquaculture Reports 7, 57-65. (Year: 2017).*

Liu, N et al. Development of a multiplex loop-mediated isothermal amplification method for the simultaneous detection of *Salmonella* spp. and *Vibrio parahaemolyticus*.2017.7:45601. (Year: 2017).*

\* cited by examiner

MULTIPLE LAMP PRIMER SET, DETECTION METHOD, AND KIT FOR SIMULTANEOUS DETECTION OF MULTIPLE PATHOGENS

CROSS-REFERENCE TO RELATED APPLICATIONS

This application claims priority to Chinese Patent Application No. 202310611140.1, filed on May 29, 2023, which is hereby incorporated by reference in its entirety.

TECHNICAL FIELD

The present disclosure relates to the field of pathogen detection technologies, and in particular, to a multiple LAMP primer set, a detection method, and a kit for simultaneously detecting multiple pathogens.

SEQUENCE LISTING

The present application contains a sequence listing which has been filed electronically in xml format and is hereby incorporated by reference in its entirety. Besides, a copy of the sequence listing in XML file is submitted later, the XML copy is created on Jan. 25, 2024, is named "MULTIPLE LAMP PRIMER SET, DETECTION METHOD, AND KIT FOR SIMULTANEOUS DETECTION OF MULTIPLE PATHOGENS-Sequence Listing" and is 17,232 bytes in size.

BACKGROUND

Grouper is a general term for a group of fish belonging to the Perciformes order, Serranidae family, and Epinephelus genus. It is mainly cultivated in coastal areas such as Guangdong, Hainan, Guangxi, Fujian, and Zhejiang in China, and is an important economic source for fishermen in southern China. In recent years, a scale of grouper aquaculture has been continuously expanding. However, with a rapid development of its aquaculture industry, a frequency of various diseases has shown a rapid upward trend, which causes large-scale fish fry and adult mortality, causes huge losses to the grouper aquaculture industry, and seriously restricts a healthy development of China's grouper industry. Viral and bacterial diseases are important types of diseases in grouper. Singapore grouper iridovirus (SGIV) is one of the main viruses that infect grouper, often causes serious economic losses to the grouper aquaculture industry. *Vibrio harveyi* and *Vibrio parahaemolyticus* are common pathogens of the *Vibrio* genus in grouper, can also pose a serious threat to the health of other important aquatic animals such as the oval pomfret and shrimp. Moreover, in recent years, grouper has often been infected with multiple pathogens simultaneously. Therefore, it is urgent to strengthen an early and rapid diagnosis and large-scale screening of pathogens and develop a multi-objective detection method for simultaneous detection of multiple pathogens.

In response to a recent situation of aquatic animals being infected by multiple pathogens simultaneously, a multiple LAMP (Loop-mediated isothermal amplification) technology has emerged. This technology has advantages of short time, simple operation, high sensitivity and specificity, and product visualization. It can also achieve simultaneous detection of multiple pathogens, greatly reducing the time for single detection of multiple pathogens. It is a promising multi-target rapid detection technology. At present, the multiple LAMP detection technology has been used in nucleic acid testing for various mammalian diseases. Although the multiple LAMP technology has so many advantages, its research on rapid detection of aquatic animal pathogens is still in its early stages, and the existing research mainly focuses on multi-target rapid detection of shrimp pathogens. There is still a significant gap in the multi-target rapid detection of grouper pathogens using multiple LAMP techniques, and there have been no reports of multi-target detection techniques that can simultaneously detect three important pathogens in the grouper (*Vibrio harveyi*, *Vibrio parahaemolyticus*, and Singapore grouper iridovirus of grouper).

SUMMARY

A purpose of the present disclosure is to overcome the shortcomings of existing technology and provide a loop-mediated isothermal amplification detection primer set, a detection method, and a kit that can simultaneously detect *Vibrio harveyi*, *Vibrio parahaemolyticus*, and Singapore grouper iridovirus, with strong specificity, easy operation, and having no need for an expensive instrument and equipment.

The present disclosure uses a loop-mediated isothermal amplification technology, takes TolC gene of *Vibrio harveyi* (GenBank accession number: APP6536.1), DNAJ gene of *Vibrio parahaemolyticus* (GenBank accession number: AWA88525.1) and RAD2 gene of grouper iridovirus (GenBank accession number: YP_164192.1) as specific target genes, designs, screens, optimizes specific primers, establishes a multiple LAMP detection method, optimizes a reaction condition, adds a positive control group and a negative control group in a reaction process, and detects an amplification product to determine whether a sample contains the *Vibrio harveyi*, the *Vibrio parahaemolyticus*, or the Singapore grouper iridovirus, so as to achieve a convenient, simple, economical, fast and sensitive detection effect, and then realizes the purpose of the present disclosure.

A first objective of the present disclosure is to provide a multiple LAMP primer set that simultaneously detects multiple pathogens, the multiple pathogens are *Vibrio harveyi*, *Vibrio parahaemolyticus*, and Singapore grouper iridovirus. The detection primer set is as shown in SEQ ID NO.: 1-18, with a specific sequence as follows:

VH-F3:
5'-TCCTTCGAGTTTCTCAAGCG-3',

VH-B3:
5'-TCACGTAGCGATTCGTAGCT-3';

VH-FIP:
5'-CTAGTTGGCGACCAACCGCTCGCGCACAAGACAACCTAG-3',

VH-BIP:
5'-TCACTGACGTACACGATGCGCCGAGTTTTCCGCCAAGACT-3';

VH-LF:
5'-GCTTTTTCTGCACGAACGAA-3',

VH-LB:
5'-AAGCACAATACGATGCAGTACTTG-3';

VP-F3:
5'-GTCTATCTGGCGAAGGCG-3',

VP-B3:
5'-ACATACGGCCAGTTTGTGTT-3';

-continued

VP-FIP:
5'-TTGCCGTCACGCTCGAAAATGTGAAATGGGTGCACCATCAGG-3'

VP BIP:
5'-AGCTTTGCTATGGCTGCACTCGCTGACGGCACTTTTAGGCT-3';

VP-LF:
5'-TGCTCTTTCACGTGTACTTGTACG-3',

VP-LB:
5'-GAAGTTGAAGTTCCAACACTTGATG-3';

SGIV-F3:
5'-AGGGACTGAAGCTGTTGCT-3';

SGIV-B3:
5'-GGATCGCCGTCAAACACAA-3';

SGIV-FIP:
5'-AGGGTCTTGCCGGAGAGCTTCAAGAGTTCAGGTGTGGAGG-3'

SGIV-BIP:
5'-ACACACAGCGTGGCAGTATCTGATAGCGTTTACGCGCCTC-3';

SGIV-LF:
5'-GTTTAGGCACACCGTAAAAT-3';

SGIV-LB:
5'-TACTGTTTATGCTGTGTTGCCTCA-3'.

A second objective of the present disclosure is to provide an application of the multiple LAMP primer set in simultaneously detecting multiple pathogens, where the multiple pathogens are the *Vibrio harveyi*, the *Vibrio parahaemolyticus*, and the Singapore grouper iridovirus, the detection is for non-disease diagnosis and non-treatment purposes.

A third objective of the present disclosure is to provide an application of the multiple LAMP primer set in a kit for simultaneous detection of multiple pathogens, the multiple pathogens are the *Vibrio harveyi*, the *Vibrio parahaemolyticus*, and the Singapore grouper iridovirus.

In an embodiment of the present disclosure, the kit includes a loop-mediated isothermal amplification reaction solution, Bst DNA polymerase, calcein solution containing MnCl$_2$, positive control sample, negative control sample, and a multiple LAMP primer set; the multiple pathogens are the *Vibrio harveyi*, the *Vibrio parahaemolyticus*, and the Singapore grouper iridovirus.

In an embodiment of the present disclosure, the positive control sample is preferably a mixture including plasmid DNA of TolC gene of the *Vibrio harveyi* (GenBank registration number APP6536.1), plasmid DNA of DNAJ gene of the *Vibrio parahaemolyticus* (GenBank registration number AWA88525.1), and plasmid DNA of RAD2 gene of the Singapore grouper iridovirus (GenBank registration number YP_164192.1); the negative control sample is ultrapure water. A fourth objective of the present disclosure is to provide a multiple LAMP detection method for simultaneously detecting multiple pathogens, which is for non-disease diagnosis and non-treatment purposes; the pathogens are the *Vibrio harveyi*, the *Vibrio parahaemolyticus*, and the Singapore grouper iridovirus; the method specifically includes the following steps:
  (1) collecting a sample, extracting genomic DNA of viruses and bacteria by virus and bacterial DNA extraction kits, mixing in an equal proportion and taking as a reaction template of LAMP;
  (2) forming a loop-mediated isothermal amplification reaction system by mixing the multiple LAMP primer set with a loop-mediated isothermal amplification reaction solution, Bst DNA polymerase, calcein solution containing MnCl$_2$ and genomic DNA of a sample, conducting a Loop-mediated isothermal amplification reaction;
  (3) detecting whether the sample contains the *Vibrio harveyi*, the *Vibrio parahaemolyticus*, or the Singapore grouper iridovirus by a calcein fluorescence colorimetric method and/or a gel electrophoresis analysis after the amplification reaction is completed.

In an embodiment of the present disclosure, the detecting whether the sample contains the *Vibrio harveyi*, the *Vibrio parahaemolyticus*, and the Singapore grouper iridovirus by a calcein fluorescence colorimetric method includes: when a color of an amplification product is bright green, the sample contains the *Vibrio harveyi*, the *Vibrio parahaemolyticus*, or the Singapore grouper iridovirus; when the color of the amplification product remains orange yellow, the sample does not contain the *Vibrio harveyi*, the *Vibrio parahaemolyticus*, or the Singapore grouper iridovirus.

In an embodiment of the present disclosure, the detecting whether the sample contains the *Vibrio harveyi*, the *Vibrio parahaemolyticus*, and the Singapore grouper iridovirus by a gel electrophoresis analysis includes: performing a gel electrophoresis on the amplification product; when there is a ladder of bands, the sample contains the *Vibrio harveyi*, the *Vibrio parahaemolyticus*, or the Singapore grouper iridovirus; when there is no ladder of bands, the sample does not contain the *Vibrio harveyi*, the *Vibrio parahaemolyticus*, or the Singapore grouper iridovirus.

A total volume of a loop-mediated isothermal amplification reaction system is 25 µL, and the loop-mediated isothermal amplification reaction system includes 2.5 µL of 10×ThermoPol Buffer, 1 µL of 100 mmol/L MgSO$_4$, 4 µL of 10 mmol/L dNTP Mix, 0.56 µL of 50 µmol/L VH-FIP, 0.56 µL of 50 µmol/L VH-BIP; 0.4 µL of 10 µmol/L VH-F3, 0.4 µL of 10 µmol/L VH-B3; 0.48 µL of 25 µmol/L VH-LF, 0.48 µL of 25 µmol/L VH-LB; 0.56 µL of 50 µmol/L VP-FIP, 0.56 µL of 50 µmol/L VP-BIP; 0.4 µL of 10 µmol/L VP-F3, 0.4 µL of 10 µmol/L VP-B3; 0.48 µL of 25 µmol/L VP-LF, 0.48 µL of 25 µmol/L VP-LB; 0.48 µL of 50 µmol/L SGIV-FIP, 0.48 µL of 50 µmol/L SGIV-BIP; 0.4 µL of 10 µmol/L SGIV-F3, 0.4 µL of 10 µmol/L SGIV-B3; 0.48 µL of 25 µmol/L SGIV-LF, 0.48 µL of 25 µmol/L SGIV-LB; 1 µL of 8 U Bst DNA polymerase, 1.5 µL of 100 mmol/L betaine; 0.5 µL of 0.5 mmol/L calcein solution with a concentration of 20 mmol/L MnCl$_2$ and 1 µL of genomic DNA template, a remaining amount is deionized water.

A reaction condition for the loop-mediated isothermal amplification reaction is: reaction at 62° C. for 30 minutes, and termination at 80° C. for 5 minutes. The beneficial effects of the present disclosure compared to prior art: the present disclosure designs a specific primer set based on the TolC gene of the *Vibrio harveyi*, the DNAJ gene of the *Vibrio parahaemolyticus*, and the RAD2 gene of the Singapore grouper iridovirus, which has good specificity and can simultaneously detect the *Vibrio harveyi*, the *Vibrio parahaemolyticus*, and the Singapore grouper iridovirus. The present disclosure designs and screens a set of specific detection primer sets, a detection kit containing the primer set, and a detection method using a loop-mediated isothermal amplification with the detection kit to determine the presence of the *Vibrio harveyi*, the *Vibrio parahaemolyticus*, and the Singapore grouper iridovirus in a detection sample. The detection primer set, detection kit, and detection method of the present disclosure have strong specificity, convenient and simple operation, short detection time, and having no need for an expensive instrument and equipment. They can simultaneously detect whether the sample contains three pathogens: *Vibrio harveyi*, *Vibrio parahaemolyticus*, and Singapore grouper iridovirus. They are particularly suitable for on-site detection at the grassroots level and have broad application prospects.

DESCRIPTION OF EMBODIMENTS

Figure 1:
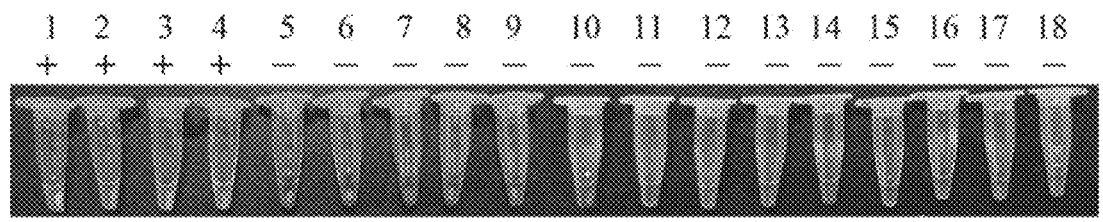
FIG. 1 is a diagram of a colorimetric analysis result of a LAMP amplification product in the specificity experiment; 1: a mixture containing recombinant plasmids of TolC gene of *Vibrio harveyi*, recombinant plasmids of DNAJ gene of *Vibrio parahaemolyticus*, and recombinant plasmids of RAD2 gene of Singapore grouper iridovirus; 2: *Vibrio harveyi*; 3: *Vibrio parahaemolyticus*; 4: Singapore grouper iridovirus; 5: *Vibrio alginolyticus*; 6: *Vibrio cholerae*; 7: *Vibrio vulnificus*; 8: *Vibrio mimicus*; 9: *Vibrio alfacsensis*; 10: *Vibrio campbellii*; 11: *Vibrio owensii*, 12: *Staphylococcus aureus*; 13: Nervous necrosis virus; 14: Infectious spleen and kidney necrosis virus; 15: Shrimp hemocyte iridescent virus; 16: Infectious hypodermal and hematopoietic necrosis virus; 17: White spot syndrome virus; 18: ultra-pure water; 1-4 bright green, and 5-18 orange yellow.

The following embodiments are further explanations of the present disclosure, do not make limitations to the present disclosure.

Example 1: Design and Synthesis of Primers

According to a design principle of loop-mediated isothermal amplification primers, target gene sequences suitable for loop-mediated isothermal amplification of *Vibrio harveyi*, *Vibrio parahaemolyticus*, and Singapore grouper iridovirus were searched in the GenBank database. Finally, TolC gene of *Vibrio harveyi* with strong specificity was selected (GenBank login number: APP6536.1), DNAJ gene of *Vibrio parahaemolyticus* (GenBank registration number AWA88525.1) and RAD2 gene of Singapore grouper iridovirus (GenBank registration number YP_164192.1) are target genes. Based on specific regions of specific genes and following the principle of loop-mediated isothermal amplification primer design, multiple sets of primers were designed using LAMP primer explore V4 primer design software, and a set of primers with best specificity was selected.

The designed multiple loop-mediated isothermal amplification detection primers are:

```
VH-F3:
5'-TCCTTCGAGTTTCTCAAGCG-3',

VH-B3:
5'-TCACGTAGCGATTCGTAGCT-3';

VH-FIP:
5'-CTAGTTGGCGACCAACCGCTCGCGCACAAGACAACCTAG-3',

VH-BIP:
5'-TCACTGACGTACACGATGCGCCGAGTTTTCCGCCAAGACT-3';

VH-LF:
5'-GCTTTTTCTGCACGAACGAA-3',

VH-LB:
5'-AAGCACAATACGATGCAGTACTTG-3';

VP-F3:
5'-GTCTATCTGGCGAAGGCG-3',

VP-B3:
5'-ACATACGGCCAGTTTGTGTT-3';

VP-FIP:
5'-TTGCCGTCACGCTCGAAAATGTGAAATGGGTGCACCATCAGG-3'

VP BIP:
5'-AGCTTTGCTATGGCTGCACTCGCTGACGGCACTTTTAGGCT-3';

VP-LF:
5'-TGCTCTTTCACGTGTACTTGTACG-3',

VP-LB:
5'-GAAGTTGAAGTTCCAACACTTGATG-3';

SGIV-F3:
5'-AGGGACTGAAGCTGTTGCT-3';

SGIV-B3:
5'-GGATCGCCGTCAAACACAA-3';

SGIV-FIP:
5'-AGGGTCTTGCCGGAGAGCTTCAAGAGTTCAGGTGTGGAGG-3'

SGIV-BIP:
5'-ACACACAGCGTGGCAGTATCTGATAGCGTTTACGCGCCTC-3';

SGIV-LF:
5'-GTTTAGGCACACCGTAAAAT-3';

SGIV-LB:
5'-TACTGTTTATGCTGTGTTGCCTCA-3'.
```

Example 2: Nucleic Acid Extraction

*Vibrio harveyi*, *Vibrio parahaemolyticus*, *Vibrio alginolyticus*, *Vibrio cholerae*, *Vibrio vulnificus*, *Vibrio mimicus*, *Vibrio alfacsensis*, *Vibrio campbellii* and *Vibrio owensii* are inoculated into LB liquid culture medium, incubated overnight at 30° C.; *Staphylococcus aureus* was separately inoculated into LB liquid culture medium and incubated overnight at 37° C. Genomic DNA of each bacterial strain was extracted with a bacterial genomic DNA extraction kit and taken as a template for LAMP amplification reaction. Viral genomic DNA was extracted with a virus genome DNA extraction kit from tissue samples respectively containing Singapore grouper iridovirus, Nervous necrosis virus, Infectious spleen and kidney necrosis virus, Shrimp hemocyte iridescent virus, Infectious hypodermal and hematopoietic necrosis virus, White spot syndrome virus, and taken as a template for LAMP amplification reaction.

Example 3: Construction of TolC, DNAJ, and RAD2 Recombinant Plasmids

Recombinant plasmid DNA of TolC gene of *Vibrio harveyi*, DNAJ gene of *Vibrio parahaemolyticus*, and RAD2 gene of Singapore grouper iridovirus, respectively constructed. A reparation method is to use T1 simple vector as a vector, and use TolC gene of *Vibrio harveyi*, DNAJ gene of *Vibrio parahaemolyticus*, and RAD2 gene of Singapore grouper iridovirus as target DNA fragments. TolC, DNAJ, and RAD2 target fragments are connected to T1 simple vector by ligases, respectively; recombinant plasmids T1-Tic, T1-DNAJ, and T1-RAD2 are constructed and transformed into *Escherichia coli* DH5a competent cell, positive clones were screened using 100 mg/mL ampicillin, and recombinant plasmid was extracted using a plasmid extraction kit. Finally, PCR detection was performed, and sequencing was performed to determine whether the recombinant plasmid was successfully constructed.

Example 4: Specificity of LAMP Method

A loop-mediated isothermal amplification reaction system of a sample is 25 µL, which includes 2.5 µL of 10×ThermoPol Buffer, 1 µL of 100 mmol/L MgSO$_4$, 4 µL of 10 mmol/L dNTP Mix, 0.56 µL of 50 µmol/L VH-FIP, 0.56 µL of 50 µmol/L VH-BIP; 0.4 µL of 10 µmol/L VH-F3, 0.4 µL of 10 µmol/L VH-B3; 0.48 µL of 25 µmol/L VH-LF; 0.48 µL of 25 µmol/L VH-LB; 0.56 µL of 50 µmol/L VP-FIP; 0.56 µL of 50 µmol/L VP-BIP; 0.4 µL of 10 µmol/L VP-F3; 0.4 µL of 10 µmol/L VP-B3; 0.48 µL of 25 µmol/L VP-LF; 0.48 µL of 25 µmol/L VP-LB; 0.48 µL of 50 µmol/L SGIV-FIP; 0.48 µL of 50 µmol/L SGIV-BIP; 0.4 µL of 10 µmol/L SGIV-F3; 0.4 µL of 10 µmol/L SGIV-B3; 0.48 µL of 25 µmol/L SGIV-LF; 0.48 µL of 25 µmol/L SGIV-LB; 1 µL of 8 U Bst DNA polymerase; 1.5 µL of 100 mmol/L betaine; 0.5 µL of 0.5 mmol/L calcein solution with a concentration of 20 mmol/L MnCl$_2$ and 1 µL of genomic DNA template (genomic DNA respectively obtained from Example 2), deionized water was filled up to 25 µL.

A loop-mediated isothermal amplification system for positive control samples is 25 µL, which included 2.5 µL of 10×ThermoPol Buffer, 1 µL of 100 mmol/L MgSO$_4$, 4 µL of 10 mmol/L dNTP Mix, 0.56 µL of 50 mol/L VH-FIP, 0.56 µL of 50 mol/L VH-BIP, 0.4 µL of 10 µmol/L VH-F3, 0.4 µL of 10 µmol/L VH-B3, 0.48 µL of 25 µmol/L VH-LF, 0.48 µL of 25 µmol/L VH-LB, 0.56 µL of 50 µmol/L VP-FIP, 0.56 µL of 50 µmol/L VP-BIP, 0.40 µL of 10 µmol/L VP-F3, 0.40 µL of 10 µmol/L VP-B3, 0.48 µL of 25 µmol/L VP-LF, 0.48 µL of 25 µmol/L VP-LB; 0.48 µL of 50 µmol/L SGIV-FIP, 0.48 µL of 50 µmol/L SGIV-BIP; 0.4 µL of 10 µmol/L SGIV-F3, 0.4 µL of 10 µmol/L SGIV-B3; 0.48 µL of 25 µmol/L SGIV-LF, 0.48 µL of 25 µmol/L SGIV-LB, 1 µL of 8 U Bst DNA polymerase, 1.5 µL of 100 mmol/L betaine, 0.5 L of 0.5 mmol/L calcein solution with a concentration of 20 mmol/L MnCl$_2$, 1 µL of a mixture solution of artificially constructed plasmids of T1-Tic, T1-DNAJ, and T1-RAD2, deionized water was filled up to 25 µL.

A loop-mediated isothermal amplification reaction system for negative control samples is 25 µL, which includes 2.5 µL of 10×ThermoPol Buffer, 1 µL of 100 mmol/L MgSO$_4$, 4 µL of 10 mmol/L dNTP Mix, 0.56 µL of 50 µmol/L VH-FIP, 0.56 µL of 50 µmol/L VH-BIP, 0.4 µL of 10 µmol/L VH-F3, 0.4 µL of 10 µmol/L VH-B3, 0.48 µL of 25 µmol/L VH-LF, 0.48 µL of 25 µmol/L VH-LB, 0.56 µL of 50 µmol/L VP-FIP, 0.56 µL of 50 µmol/L VP-BIP, 0.4 µL of 10 µmol/L VP-F3, 0.4 µL of 10 µmol/L VP-B3, 0.48 µL of 25 µmol/L VP-LF, 0.48 µL of 25 µmol/L VP-LB, 0.48 µL of 50 µmol/L SGIV-FIP, 0.48 µL of 50 µmol/L SGIV-BIP, 0.4 µL of 10 µmol/L SGIV-F3, 0.4 µL of 10 µmol/L SGIV-B3, 0.48 µL of 25 µmol/L SGIV-LF, 0.48 µL of 25 µmol/L SGIV-LB, 1 µL of 8 U Bst DNA polymerase, 1.5 µL of 100 mmol/L betaine, 0.5 µL of 5 mmol/L calcein solution with a concentration of 20 mmol/L MnCl$_2$ and 1 µL of ultrapure water, deionized water was filled up to 25 µL.

The above three loop-mediated isothermal amplification systems were evenly mixed and placed in a constant temperature water bath under a reaction condition of 62° C. for 30 minutes; the reaction was terminated at 80° C. for 5 minutes.

Calcein solution (containing MnCl$_2$) was added to the reaction system. After the reaction is completed, whether the color of the reaction product has changed was observed. If the color is bright green, it is positive; and if the color is orange, it is negative. As shown in FIG. 1, the detection results of calcein fluorescence colorimetric method show that amplified products of *Vibrio harveyi*, *Vibrio parahaemolyticus*, Singapore grouper iridovirus, and the positive control sample are bright green and positive; the amplification reaction products of *Vibrio alginolyticus*, *Vibrio cholerae*, *Vibrio vulnificus*, *Vibrio mimicus*, *Vibrio alfacsensis*, *Vibrio campbellii* and *Vibrio owensii*, *Staphylococcus aureus*, Nervous necrosis virus, Infectious spleen and kidney necrosis virus, Shrimp hemocyte iridescent virus, Infectious hypodermal and hematopoietic necrosis virus, White spot syndrome virus and ultra-pure water are orange yellow and negative.

Figure 2:
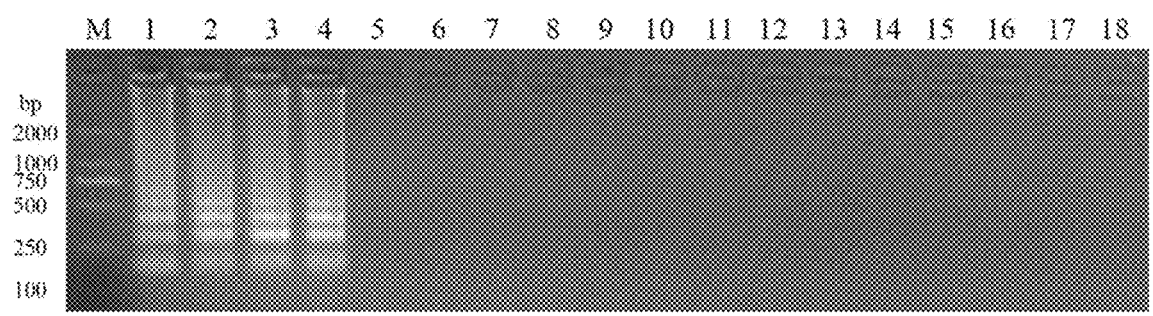
FIG. 2 is diagram of a gel electrophoresis result of the LAMP amplification product in the specificity experiment; M: Standard molecular weight DL2000; 1: a mixture containing recombinant plasmids of TolC gene of *Vibrio harveyi*, recombinant plasmids of DNAJ gene of *Vibrio parahaemolyticus*, and recombinant plasmids of RAD2 gene of Singapore grouper iridovirus; 2: *Vibrio harveyi*; 3: *Vibrio parahaemolyticus*; 4: Singapore grouper iridovirus; 5: *Vibrio alginolyticus*; 6: *Vibrio cholerae*; 7: *Vibrio vulnificus*; 8: *Vibrio mimicus*; 9: *Vibrio alfacsensis*; 10: *Vibrio campbellii*; 11: *Vibrio owensii*; 12: *Staphylococcus aureus*; 13: Nervous necrosis virus; 14: Infectious spleen and kidney necrosis virus; 15: Shrimp hemocyte iridescent virus; 16: Infectious hypodermal and hematopoietic necrosis virus; 17: White spot syndrome virus; 18: ultra-pure water.

After the loop-mediated isothermal amplification reaction is completed, 5 µL of amplification product was taken and spot sampled on 2% agarose gel for electrophoresis detection, and 180 V was energized for 20 min, as shown in FIG. 2. The electrophoresis analysis and detection results showed that the amplification products of *Vibrio harveyi*, *Vibrio parahaemolyticus*, Singapore grouper iridovirus and positive control samples showed specific ladder of bands (positive); however, the electrophoretic results of *Vibrio alginolyticus*, *Vibrio cholerae*, *Vibrio vulnificus*, *Vibrio mimicus*, *Vibrio alfacsensis*, *Vibrio campbellii* and *Vibrio owensii*, *Staphylococcus aureus*, Nervous necrosis virus, Infectious spleen and kidney necrosis virus, Shrimp hemocyte iridescent virus, Infectious hypodermal and hematopoietic necrosis virus, White spot syndrome virus and ultra-pure water showed no specific bands (negative). This indicates that the multiple loop-mediated isothermal amplification detection primer set of the present disclosure has high specificity and strong specificity, can be used for rapid detection of whether a sample contains the *Vibrio harveyi*, the *Vibrio parahaemolyticus*, and the Singapore grouper iridovirus simultaneously.

Example 5: Sensitivity of LAMP Method

The extracted recombinant plasmids of T1-TolC, T1-DNAJ, and T1-RAD2 were diluted to same concentration and mixed in a 1:1:1 equal volume until a final concentration of the mixed plasmids is 1 μg/ml, then ddH$_2$O at a 10 fold gradient was diluted to 1 fg/ml, 10 fg/ml, 100 fg/ml, 1 pg/ml, 10 pg/ml, 100 pg/ml, 1 ng/ml, 10 ng/ml, and 100 ng/ml, respectively, and taken as DNA templates for LAMP sensitivity detection.

A loop-mediated isothermal amplification reaction system for LAMP sensitivity detection is 25 μL, which includes: 2.5 μL of 10×ThermoPol Buffer, 1 μL of 100 mmol/L MgSO$_4$, 4 μL of 10 mmol/L dNTP Mix, 0.56 μL of 50 μmol/L VH-FIP, 0.56 μL of 50 μmol/L VH-BIP, 0.4 μL of 10 μmol/L VH-F3, 0.4 μL of 10 μmol/L VH-B3, 0.48 μL of 25 μmol/L VH-LF, 0.48 μL of 25 μmol/L VH-LB, 0.56 μL of 50 μmol/L VP-FIP, 0.56 μL of 50 μmol/L VP-BIP, 0.4 μL of 10 μmol/L VP-F3, 0.4 μL of 10 μmol/L VP-B3, 0.48 μL of 25 μmol/L VP-LF, 0.48 μL of 25 μmol/L VP-LB, 0.48 μL of 50 μmol/L SGIV-FIP, 0.48 μL of 50 μmol/L SGIV-BIP, 0.4 μL of 10 μmol/L SGIV-F3, 0.4 μL of 10 μmol/L SGIV-B3, 0.48 μL of 25 μmol/L SGIV-LF, 0.48 μL of 25 μmol/L SGIV-LB, 1 μL of 8 U Bst DNA polymerase, 1.5 μL of 100 mmol/L betaine, 0.5 μL of 0.5 mmol/L calcein solution with a concentration of 20 mmol/L MnCl$_2$ and 1 μL plasmid mixtures of various dilution concentrations, deionized water was filled up to 25 μL.

After the LAMP amplification system was mixed evenly, placed in a constant temperature water bath under a reaction condition of 62° C. for 30 minutes, the reaction was terminated at 80° C. for 5 minutes.

Figure 3:
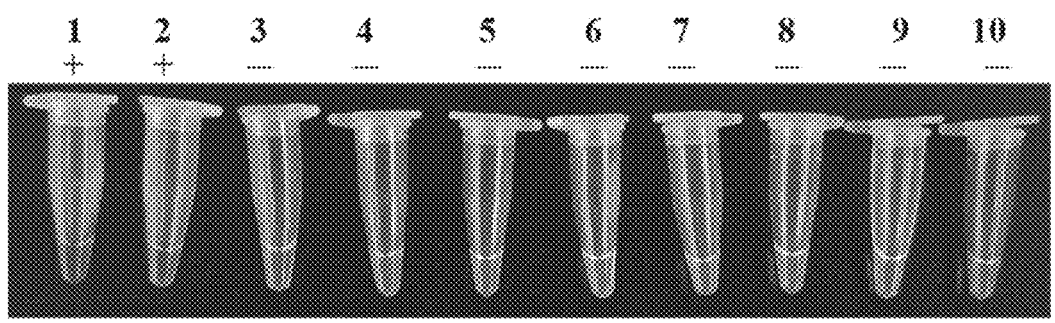
FIG. 3 is a diagram of a color analysis result of the LAMP amplification product in the sensitivity experiment; 1:1 fg/ml; 2:10 fg/ml, 3:100 fg/ml, 4:1 pg/ml, 5:10 pg/ml, 6:100 pg/ml, 7:1 ng/ml, 8:10 ng/ml, 9:100 ng/ml, 10: a mixture containing recombinant plasmids of TolC gene of *Vibrio harveyi*, recombinant plasmids of DNAJ gene of *Vibrio parahaemolyticus*, and recombinant plasmids of RAD2 gene of Singapore grouper iridovirus.
Figure 4:
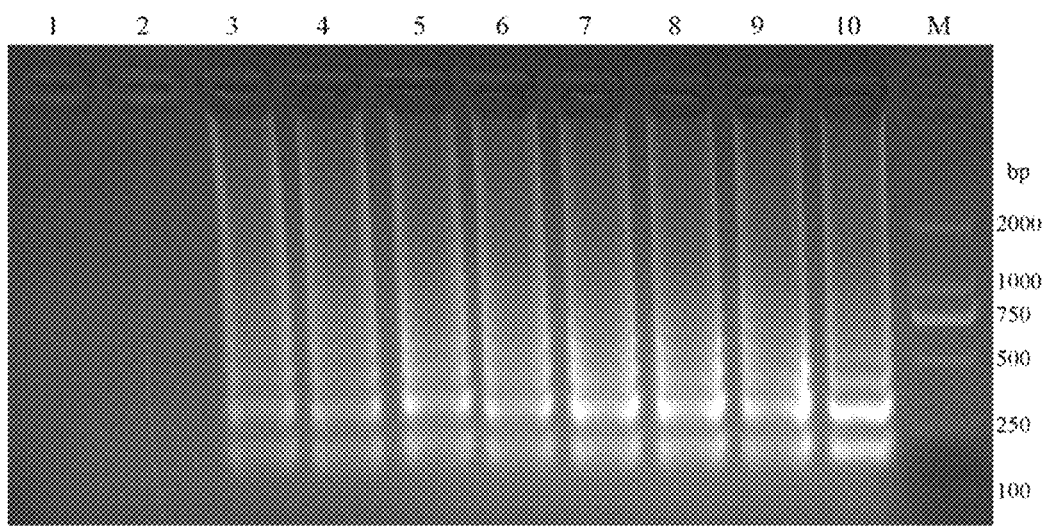
FIG. 4 is a diagram of a gel electrophoresis result of the LAMP amplification product in the sensitivity experiment; 1:1 fg/ml; 2:10 fg/ml, 3:100 fg/ml, 4:1 pg/ml, 5:10 pg/ml, 6:100 pg/ml, 7:1 ng/ml, 8:10 ng/ml, 9:100 ng/ml, 10: a mixture containing recombinant plasmids of TolC gene of *Vibrio harveyi*, recombinant plasmids of DNAJ gene of *Vibrio parahaemolyticus*, and recombinant plasmids of RAD2 gene of Singapore grouper iridovirus; M: Standard molecular weight DL2000.

As shown in FIGS. 3 and 4, the sensitivity of loop-mediated isothermal amplification detection method of the present disclosure is 100 fg/ml. The fluorescence colorimetric detection result of calcein pigment is 100 fg/ml~100 ng/ml, which is bright green (positive), while 1 fg/ml and 10 fg/ml are orange yellow (negative); 2% gel electrophoresis showed that there were specific bands (positive) in 100 fg/ml~100 ng/ml, and no specific bands (negative) in 1 fg/ml and 10 fg/ml; the detection result of fluorescence color method (FIG. 3) is consistent with that of the gel electrophoresis (FIG. 4), which indicates that the sensitivity of the multiple loop-mediated isothermal amplification detection method of the present disclosure is 100 fg/ml.

The results of calcein fluorescence color method and gel electrophoresis analysis are consistent, which proves that the data of this method is reliable. The presence of *Vibrio harveyi*, *Vibrio parahaemolyticus*, and Singapore grouper iridovirus in the sample can be directly determined by the color of the amplification product, greatly reducing the detection time.

In summary, the multiplex loop-mediated isothermal amplification detection primer set and detection method of *Vibrio harveyi*, *Vibrio parahaemolyticus*, and Singapore grouper iridovirus of the present disclosure can not only quickly, conveniently, and sensitively detect the *Vibrio harveyi*, the *Vibrio parahaemolyticus*, and the Singapore grouper iridovirus, but also have strong specificity and high accuracy.

What is claimed is:

1. A multiple LAMP primer set that simultaneously detects multiple pathogens, wherein the multiple pathogens are *Vibrio harveyi, Vibrio parahaemolyticus*, and Singapore grouper iridovirus; the multiple LAMP primer set is shown in SEQ ID NO.: 1-18.

2. A detection method for the multiple LAMP primer set as claimed in claim 1, wherein the detection method simultaneously detects multiple pathogens and is for non-disease diagnosis and non-treatment purposes, the multiple pathogens are *Vibrio harveyi, Vibrio parahaemolyticus*, and Singapore grouper iridovirus; the detection method comprises the following steps:

(1) collecting a sample, extracting genomic DNA of viruses and bacteria by virus and bacterial DNA extraction kits, mixing in an equal proportion and taking as a reaction template of LAMP;

(2) forming a loop-mediated isothermal amplification reaction system by mixing the multiple LAMP primer set with a loop-mediated isothermal amplification reaction solution, Bst DNA polymerase, calcein solution containing $MnCl_2$ and genomic DNA of a sample, conducting a loop-mediated isothermal amplification reaction;

wherein a reaction condition for the loop-mediated isothermal amplification reaction is: reaction at 62° C. for 30 minutes, and termination at 80° C. for 5 minutes;

(3) detecting whether the sample contains *Vibrio harveyi, Vibrio parahaemolyticus*, or Singapore grouper iridovirus by a calcein fluorescence colorimetric method and/or a gel electrophoresis analysis after the amplification reaction is completed.

\* \* \* \* \*

SEQUENCE LISTING

```
Sequence total quantity: 18
SEQ ID NO: 1             moltype = DNA  length = 20
FEATURE                  Location/Qualifiers
source                   1..20
                         mol_type = other DNA
                         organism = Synthetic construct
SEQUENCE: 1
tccttcgagt ttctcaagcg                                                 20

SEQ ID NO: 2             moltype = DNA  length = 20
FEATURE                  Location/Qualifiers
source                   1..20
                         mol_type = other DNA
                         organism = Synthetic construct
SEQUENCE: 2
tcacgtagcg attcgtagct                                                 20

SEQ ID NO: 3             moltype = DNA  length = 39
FEATURE                  Location/Qualifiers
source                   1..39
                         mol_type = other DNA
                         organism = Synthetic construct
SEQUENCE: 3
ctagttggcg accaaccgct cgcgcacaag acaacctag                            39

SEQ ID NO: 4             moltype = DNA  length = 40
FEATURE                  Location/Qualifiers
source                   1..40
                         mol_type = other DNA
                         organism = Synthetic construct
SEQUENCE: 4
tcactgacgt acacgatgcg ccgagttttc cgccaagact                           40

SEQ ID NO: 5             moltype = DNA  length = 20
FEATURE                  Location/Qualifiers
source                   1..20
                         mol_type = other DNA
                         organism = Synthetic construct
SEQUENCE: 5
gcttttctg cacgaacgaa                                                  20

SEQ ID NO: 6             moltype = DNA  length = 24
```

```
FEATURE                 Location/Qualifiers
source                  1..24
                        mol_type = other DNA
                        organism = Synthetic construct
SEQUENCE: 6
aagcacaata cgatgcagta cttg                                              24

SEQ ID NO: 7            moltype = DNA   length = 18
FEATURE                 Location/Qualifiers
source                  1..18
                        mol_type = other DNA
                        organism = Synthetic construct
SEQUENCE: 7
gtctatctgg cgaaggcg                                                     18

SEQ ID NO: 8            moltype = DNA   length = 20
FEATURE                 Location/Qualifiers
source                  1..20
                        mol_type = other DNA
                        organism = Synthetic construct
SEQUENCE: 8
acatacggcc agtttgtgtt                                                   20

SEQ ID NO: 9            moltype = DNA   length = 42
FEATURE                 Location/Qualifiers
source                  1..42
                        mol_type = other DNA
                        organism = Synthetic construct
SEQUENCE: 9
ttgccgtcac gctcgaaaat gtgaaatggg tgcaccatca gg                          42

SEQ ID NO: 10           moltype = DNA   length = 41
FEATURE                 Location/Qualifiers
source                  1..41
                        mol_type = other DNA
                        organism = Synthetic construct
SEQUENCE: 10
agctttgcta tggctgcact cgctgacggc acttttaggc t                           41

SEQ ID NO: 11           moltype = DNA   length = 24
FEATURE                 Location/Qualifiers
source                  1..24
                        mol_type = other DNA
                        organism = Synthetic construct
SEQUENCE: 11
tgctctttca cgtgtacttg tacg                                              24

SEQ ID NO: 12           moltype = DNA   length = 25
FEATURE                 Location/Qualifiers
source                  1..25
                        mol_type = other DNA
                        organism = Synthetic construct
SEQUENCE: 12
gaagttgaag ttccaacact tgatg                                             25

SEQ ID NO: 13           moltype = DNA   length = 19
FEATURE                 Location/Qualifiers
source                  1..19
                        mol_type = other DNA
                        organism = Synthetic construct
SEQUENCE: 13
agggactgaa gctgttgct                                                    19

SEQ ID NO: 14           moltype = DNA   length = 19
FEATURE                 Location/Qualifiers
source                  1..19
                        mol_type = other DNA
                        organism = Synthetic construct
SEQUENCE: 14
ggatcgccgt caaacacaa                                                    19

SEQ ID NO: 15           moltype = DNA   length = 40
FEATURE                 Location/Qualifiers
source                  1..40
                        mol_type = other DNA
                        organism = Synthetic construct
SEQUENCE: 15
agggtcttgc cggagagctt caagagttca ggtgtggagg                             40
```

```
SEQ ID NO: 16          moltype = DNA  length = 40
FEATURE                Location/Qualifiers
source                 1..40
                       mol_type = other DNA
                       organism = Synthetic construct
SEQUENCE: 16
acacacagcg tggcagtatc tgatagcgtt tacgcgcctc                              40

SEQ ID NO: 17          moltype = DNA  length = 20
FEATURE                Location/Qualifiers
source                 1..20
                       mol_type = other DNA
                       organism = Synthetic construct
SEQUENCE: 17
gtttaggcac accgtaaaat                                                    20

SEQ ID NO: 18          moltype = DNA  length = 24
FEATURE                Location/Qualifiers
source                 1..24
                       mol_type = other DNA
                       organism = Synthetic construct
SEQUENCE: 18
tactgtttat gctgtgttgc ctca                                               24
```